United States Patent
Niddam-Hildesheim et al.

(10) Patent No.: US 7,612,203 B2
(45) Date of Patent: *Nov. 3, 2009

(54) ROSUVASTATIN AND SALTS THEREOF FREE OF ROSUVASTATIN ALKYLETHER AND A PROCESS FOR THE PREPARATION THEREOF

(75) Inventors: Valerie Niddam-Hildesheim, Ein Vered (IL); Anna Balanov, Rehovot (IL); Natalia Shenkar, Petach Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/360,289

(22) Filed: Feb. 22, 2006

(65) Prior Publication Data

US 2006/0258882 A1 Nov. 16, 2006

Related U.S. Application Data

(60) Provisional application No. 60/655,580, filed on Feb. 22, 2005, provisional application No. 60/676,388, filed on Apr. 28, 2005, provisional application No. 60/723,491, filed on Oct. 3, 2005, provisional application No. 60/723,875, filed on Oct. 4, 2005, provisional application No. 60/732,979, filed on Nov. 2, 2005, provisional application No. 60/751,079, filed on Dec. 15, 2005, provisional application No. 60/760,506, filed on Jan. 19, 2006, provisional application No. 60/762,348, filed on Jan. 25, 2006.

(51) Int. Cl.
*C07D 239/00* (2006.01)
*C07D 239/02* (2006.01)

(52) U.S. Cl. .................................... 544/242

(58) Field of Classification Search ............. None
See application file for complete search history.

(56) References Cited

U.S. PATENT DOCUMENTS

| | | | |
|---|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 4,739,073 A | 4/1988 | Kathawala |
| 5,006,530 A | 4/1991 | Angerbauer et al. |
| 5,177,080 A | 1/1993 | Angerbauer et al. |
| 5,202,029 A | 4/1993 | Haytko et al. |
| 5,260,440 A | 11/1993 | Hirai et al. |
| 5,354,772 A | 10/1994 | Kathawala |
| 5,354,879 A | 10/1994 | Konoike et al. |
| RE37,314 E | 8/2001 | Hirai et al. |
| 6,316,460 B1 | 11/2001 | Creekmore et al. |
| 6,333,198 B1 | 12/2001 | Edmeades et al. |
| 6,777,552 B2 | 8/2004 | Niddam-Hildesheim et al. |
| 6,858,618 B2 | 2/2005 | Raza et al. |
| 2005/0080134 A1 | 4/2005 | Niddam-Hildesheim et al. |
| 2005/0131066 A1 | 6/2005 | Niddam-Hildesheim et al. |
| 2005/0159615 A1 | 7/2005 | Lifshitz-Liron et al. |
| 2005/0222415 A1 | 10/2005 | Kumar et al. |
| 2006/0258882 A1 | 11/2006 | Niddam-Hildesheim et al. |
| 2007/0037979 A1 | 2/2007 | Niddam-Hildesheim et al. |
| 2007/0179166 A1 | 8/2007 | Niddam-Hildesheim et al. |

FOREIGN PATENT DOCUMENTS

| | | |
|---|---|---|
| CN | 1 872 841 | 12/2006 |
| EP | 0 554 455 | 8/1993 |
| EP | 0 850 902 | 7/1998 |
| EP | 0 521 471 | 10/2000 |
| EP | 1 816 126 | 8/2007 |
| JP | 07 118233 | 5/1995 |
| WO | WO 00/17150 | 3/2000 |
| WO | WO 00/49014 A | 8/2000 |
| WO | WO 01/60804 | 8/2001 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 | 2/2004 |
| WO | WO 2004/052867 | 6/2004 |
| WO | WO 2005/021511 | 3/2005 |
| WO | WO 2005/023778 | 3/2005 |
| WO | WO 2005/040134 | 5/2005 |
| WO | WO 2005/056534 | 6/2005 |
| WO | WO 2005/077916 | 8/2005 |
| WO | WO 2006/035277 | 4/2006 |
| WO | WO 2006/067456 | 6/2006 |
| WO | WO 2006/079611 | 8/2006 |

(Continued)

OTHER PUBLICATIONS

Anelli, et al., "Fast And Selective Oxidation Of Primary Alcohols To Aldehydes Or To Carboxylic Acids And Of Secondary Alcohols To Ketones Mediated By Oxoammonium Salts Under Two-Phase Conditions", *J. Org. Chem.*, 1987, pp. 2559-2562, vol. 52, No. 12.

(Continued)

*Primary Examiner*—James O Wilson
*Assistant Examiner*—Noble Jarrell
(74) *Attorney, Agent, or Firm*—Kenyon & Kenyon LLP

(57) ABSTRACT

The present invention provides rosuvastatin and intermediates thereof having a low level of alkylether impurity and processes for the preparation thereof.

24 Claims, No Drawings

FOREIGN PATENT DOCUMENTS

| WO | WO 2006/091770 | 8/2006 |
| --- | --- | --- |
| WO | WO 2006 100689 | 9/2006 |
| WO | WO 2006/106526 | 10/2006 |
| WO | WO 2006/136407 | 12/2006 |
| WO | WO 2006/136408 | 12/2006 |
| WO | WO 2007/007119 | 1/2007 |
| WO | WO 2007/041666 | 4/2007 |
| WO | WO 2007/099561 | 9/2007 |

OTHER PUBLICATIONS

Hull, et al., "Quantification Of Rosuvastatin In Human Plasma By Automated Solid-Phase Extraction Using Tandem Mass Spectrometric Detection", *Journal of Chromatography B: Biomedical Sciences & Applications*, 2002, pp. 219-228, vol. 772, No. 2.

Konoike, et al. "Practical Synthesis of Chiral Synthons for the Preparation of HMG-CoA Reductase Inhibitors" J. Org. Chem., vol. 59, 1994, pp. 7849-7854.

Lenz, et al., "Tetra-*N*-Propylammonium Perruthenate (TPAP)-Catalysed Oxidations Of Alcohols Using Molecular Oxygen As A Co-Oxidant", *J. Chem. Soc., Perkin Trans. 1*, 1997, 3291-3292.

Ley, et al., *Synthesis*, 1994, 639-666.

Lipid Research Clinics Program, "The Lipid Research Clinics Coronary Primary Prevention Trial Results: I. Reduction In Incidence Of Coronary Heart Disease", *J.A.M.A.*, 1984, 351-74, vol. 251, No. 3.

Scandinavian Simvastatin Survival Study Group, "Randomised Trial Of Cholesterol Lowering In 4444 Patients With Coronary Heart Disease: The Scandinavian Survival Study (4s)", *The Lancet*, 1994, pp. 1383-1389, vol. 344.

Snyder, et al., *Introduction To Modern Liquid Chromatography, 2nd ed.*, John Wiley & Sons: New York, 1979, pp. 549, 552, 571-572.

Strobel, et al., *Chemical Instrumentation: A Systematic Approach, 3rd ed.*, Wiley & Sons: New York, 1989, pp. 391-393, 879, 894, 922, 924-925, 953.

Wantanabe, et al., "Synthesis And Biological Antivity Of Methanesulfonamide Pyramidine-And N-Methanesulfonyl Pyrrole-Substituted 3,5-Dihydroxy-6-Heptenoates, A Novel Series Of HMG-CoA Reductase Inhibitors", *Bioorganic & Medicinal Chemistry*, 1997, pp. 437-444, vol. 5, No. 2.

Witztum, "Chapter 36: Drugs Used In The Treatment Of Hyperlipoproteinemias", *Goodman & Gilman's The Pharmacological Basis Of Therapeutics, 9th ed.*, pp. 875-897.

Szantay, et al., "Synthesis of Novel HMG-CoA Reductase Inhibitors, Naphthalene Analogs of Mevinolin", Liebigs Ann. Chem., 1992, pp. 145-157.

Ohrlein, et al., "Chemo-Enzymatic Approach to Statin Side-Chain Building Blocks", Adv. Synth. Catal., 2003, pp. 713-715, vol. 345.

Greene, "Protective Groups in Organic Synthesis", John Wiley & Sons, Inc., 1981.

Tetrahedron, 1997, pp. 10659-10670, vol. 53 (31).

Mehta, T.N. et al, Determination Of Rosuvastatin In The Presence of Its Degradation Products By A Stability-Indicating LC Method, Journal of AOAC International, AOAC International, Arlington, VA, US, vol. 88, No. 4, Jul. 2005, pp. 1142-1147, XP008066428.

Sane, R.T. et al, Determination of Rosuvastatin Calcium In Its Bulk Drug And Pharmaceutical Preparations By High-Performance Thin-Layer Chromatography: JPC. Journal of Planar Chromatography, Moder TLC, Huethig, Heidelberg, DE, vol. 18, No. 103, May 2005, p. 194-198, XP008066430.

ROSUVASTATIN AND SALTS THEREOF FREE OF ROSUVASTATIN ALKYLETHER AND A PROCESS FOR THE PREPARATION THEREOF

RELATED APPLICATIONS

This application claims the benefit of U.S. Provisional Application No. 60/655,580, filed Feb. 22, 2005; U.S. Provisional Application No. 60/676,388, filed Apr. 28, 2005; U.S. Provisional Application No. 60/723,491, filed Oct. 3, 2005; U.S. Provisional Application No. 60/723,875, filed Oct. 4, 2005; U.S. Provisional Application No. 60/732,979 filed Nov. 2, 2005; U.S. Provisional Application No. 60/751,079, filed Dec. 15, 2005; U.S. Provisional Application No. 60/760,506, filed Jan. 19, 2006; and U.S. Provisional Application No. No. 60/762,348, filed Jan. 25, 2006.

FIELD OF THE INVENTION

The present invention relates to rosuvastatin and salts and intermediates thereof having a low level of alkylether impurity and processes for the preparation thereof.

BACKGROUND OF THE INVENTION

Rosuvastatin calcium has the chemical name (7-[4-(4-fluorophenyl)-6-isopropyl-2-(N-methyl-N-methylsulfonylamino)pyrimidin-5-yl]-(3R,5S)-dihydroxy-(E)-6-heptenoic acid-calcium salt), and has the following chemical formula:

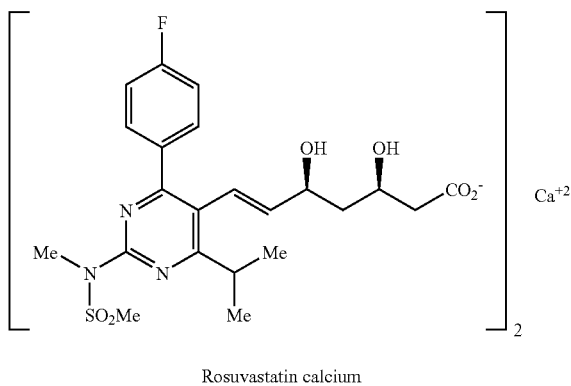

Rosuvastatin calcium

Rosuvastatin calcium is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium is a superstatin, which can lower LDL-cholesterol and triglycerides more effectively than first generation statin drugs.

Rosuvastatin calcium is marketed under the name CRESTOR for the treatment of a mammal such as a human. According to the maker of CRESTOR, it is administered in a daily dose of from about 5 mg to about 40 mg.

U.S. RE Pat. No. 37,314 discloses the preparation of Rosuvastatin calcium, wherein the step of removing the alcohol protecting group, $R_2$, of the intermediate 1

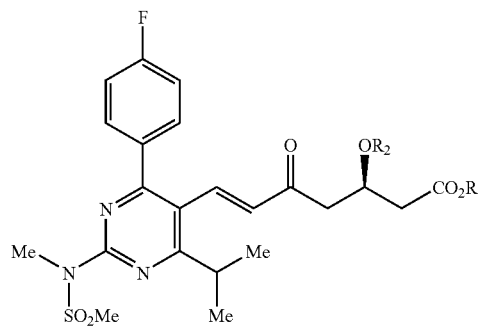

Intermediate 1 to obtain the intermediate 2

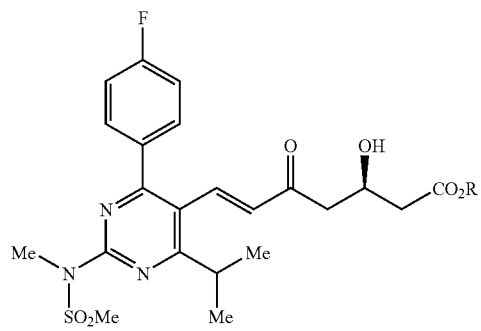

Intermediate 2 is performed by using a solution of hydrofluoric acid. However, the use of hydrofluoric acid is problematic on an industrial scale because of the strong corrosive properties and very toxic vapors; contact with glass or metal should also be avoided.

An alternative method for removing the silyl protecting group of the intermediate 1 is disclosed in U.S. patent Ser. No. 05/222,415. According to the disclosure of this application, methanesulfonic acid in methanol is used instead of hydrofluoric acid; however, this process may lead to contamination of the final product by the impurity rosuvastatin-calcium-methylether, as exemplified in example 4.

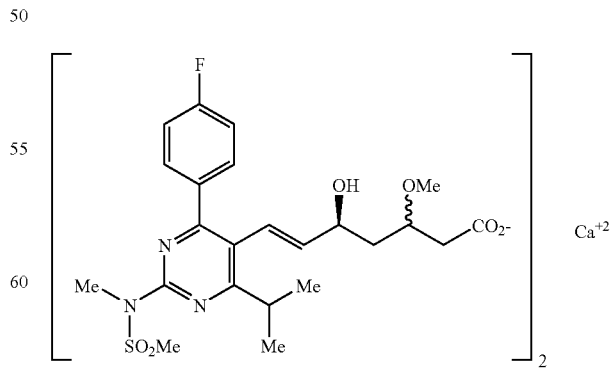

Rosuvastatin-calcium-methylether

Rosuvastatin calcium, like any synthetic compound, can contain extraneous compounds or impurities originating from various sources. These impurities in rosuvastatin calcium, or any active pharmaceutical ingredient (API), are undesirable and, in extreme cases, may even be harmful to a patient being treated with a dosage form containing the API.

Impurities in an API may arise from degradation of the API itself, which is related to the stability of the pure API during storage, and from the manufacturing process, including the chemical synthesis of the API. Process impurities include unreacted starting materials, chemical derivatives of impurities contained in starting materials, synthetic by-products of the reaction, and degradation products.

The stability of an API during storage is a critical factor in the shelf life of the API, and so affects the ability to commercialize an API. The purity of the API resulting from the manufacturing process also affects the ability to commercialize an API. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

At certain stages during processing of an API, it must be analyzed for purity because the product of a chemical reaction is rarely a single compound with sufficient purity to comply with pharmaceutical standards. Side products and by-products of the reaction and adjunct reagents used in the reaction will, in most cases, also be present in the product mixture. Typically, the API is analyzed by HPLC or TLC analysis to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position on the TLC plate (wherein the position on the plate is measured in cm from the base line of the plate) or by its relative position in the chromatogram of the HPLC (where the position in a chromatogram is conventionally measured in minutes between injection of the sample on the column and elution of the particular component through the detector). The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker or reference standard. It may be advantageous to select a compound other than the API that is added to, or present in, the mixture in an amount sufficiently large to be detectable and sufficiently low as not to saturate the column, and to use that compound as the reference marker or reference standard for determination of the RRT.

As is known by those skilled in the art, the management of process impurities is greatly enhanced by understanding their chemical structures and synthetic pathways, and by identifying the parameters that influence the amount of impurities in the final product.

In this application the impurity rosuvastatin calcium-alkylether in the API is used as the reference marker or reference standard.

There is a need in the art for rosuvastatin calcium having low levels of rosuvastatin-calcium-alkylether, and for processes of preparing rosuvastatin calcium having a lower level of rosuvastatin-calcium-methylether.

SUMMARY OF THE INVENTION

In one aspect, the present invention provides the compound of formula I-ether of the following structure,

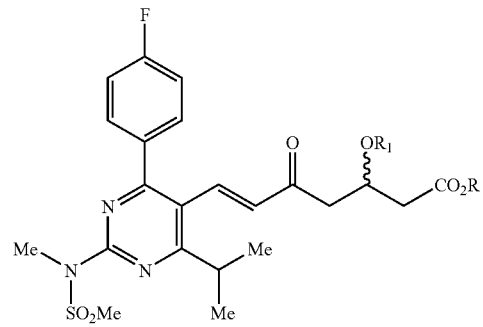

Formula I-ether wherein R is a carboxyl protecting group that is not methyl ester and $R_1$ is a $C_1$-$C_8$ linear or branched alkyl. In another aspect, the invention provides the compound of formula I-ether wherein R is a carboxyl protecting group that is not methyl ester and $R_1$ is a $C_2$-$C_8$ linear or branched alkyl.

In another aspect, the present invention provides an isolated compound of formula I-ether, wherein R is a carboxyl protecting group, and $R_1$ is a $C_2$-$C_8$ linear or branched alkyl. In a preferred aspect of the invention, $R_1$ is methyl.

In a particularly preferred aspect of the invention, R is tert-butyl carboxyl and $R_1$ is methyl, and the compound of formula I-ether corresponds to TB-21-methylether of the structure,

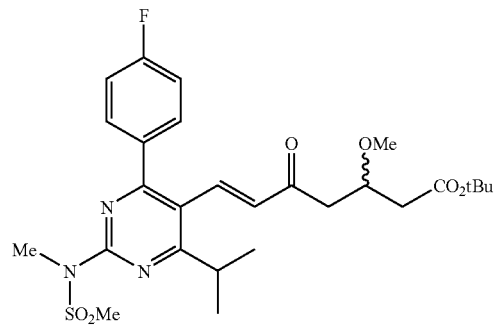

TB-21-methylether

In another aspect, the present invention provides a process for preparing the isolated compound of formula I-ether, wherein R is a carboxyl protecting group and R1 is a $C_1$-$C_8$ linear or branched alkyl.

In yet another aspect, the present invention provides the compound of formula II-ether, of the following structure, II-ether

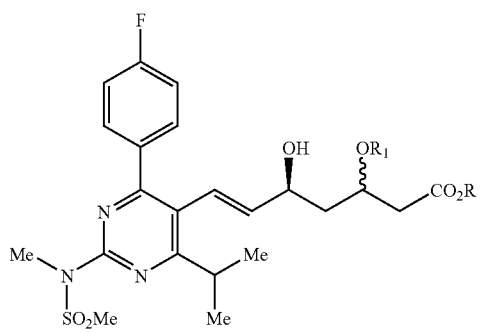

wherein R is a carboxyl protecting group and $R_1$ is a $C_1$-$C_8$ linear or branched alkyl. In another aspect, the invention provides the compound of formula I-ether wherein R is a carboxyl protecting group and $R_1$ is a $C_2$-$C_8$ linear or branched alkyl.

In a particularly preferred aspect of the invention, R is tert-butyl carboxyl and R.sub.1 is methyl, and the compound of formula II-ether corresponds to TBRE-methylether of the structure,

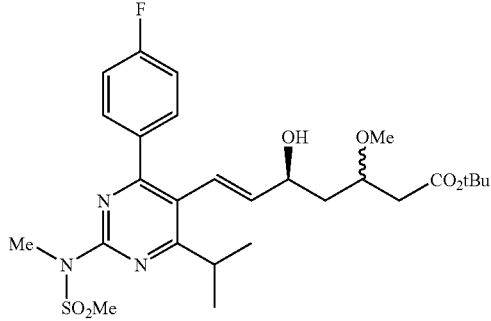

TBRE-methylether

In another aspect, the present invention provides a process for preparing the compound of formula II-ether, wherein R is as defined above and $R_1$ is a $C_1$-$C_8$ linear or branched alkyl.

In another aspect, the present invention provides the compound of formula III-ether (also referred to as Rosu-alkylether) and salts thereof, with the following structure, III-ether

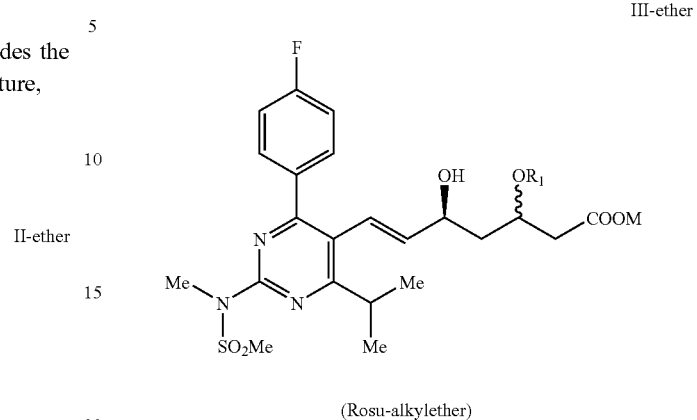

(Rosu-alkylether)

wherein $R_1$ is a $C_1$-$C_8$ linear or branched alkyl and M is either H or a metal cation. In another aspect, the invention provides the compound of formula III-ether wherein $R_1$ is a $C_2$-$C_8$ linear or branched alkyl and M is either H or a metal cation. In a preferred aspect of the invention, $R_1$ is methyl. In another preferred aspect of the invention, M is $Ca^{+2}$.

In a particularly preferred aspect of the invention, M is $Ca^{+2}$ and $R_1$ is methyl, and the compound of formula III-ether corresponds to rosuvastatin calcium methyl-ether having the structure,

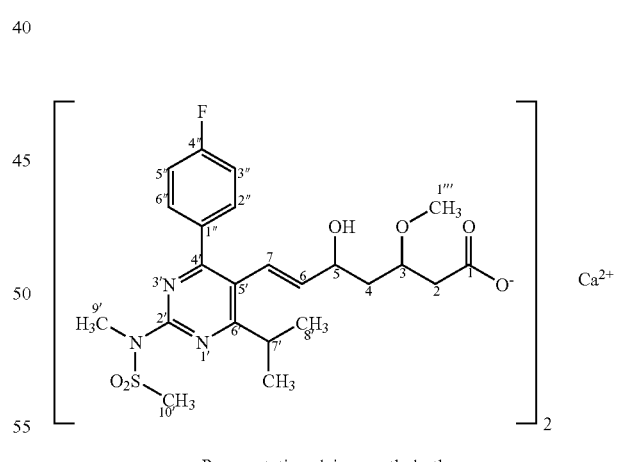

Rosuvastatin calcium methyl-ether

In another aspect, the present invention provides a process for preparing the isolated compound III-ether, wherein $R_1$ is a $C_1$-$C_8$ linear or branched alkyl and M is either H or a metal cation.

In another aspect, the present invention provides the compound of formula I,

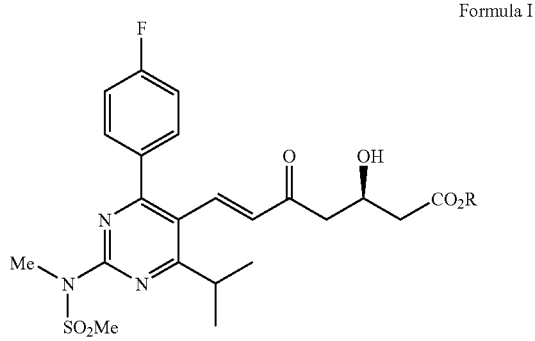

Formula I wherein R is a carboxyl protecting group, having about 0.02% to about 1.5% area by HPLC of the compound of formula I-ether.

In yet another aspect, the present invention provides the compound of formula II

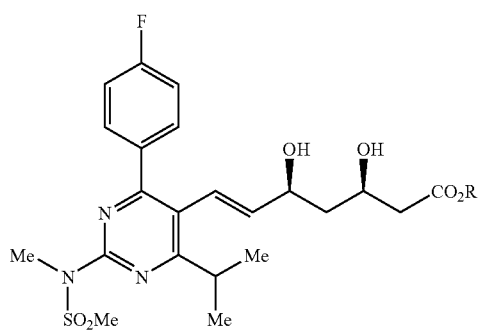

Formula II wherein R is a carboxyl protecting group, having about 0.02% to about 1.5% area by HPLC of the compound of formula II-ether.

In one aspect, the present invention provides the compound of formula III, referred to as Rosuvastatin or Rosu, Formula III

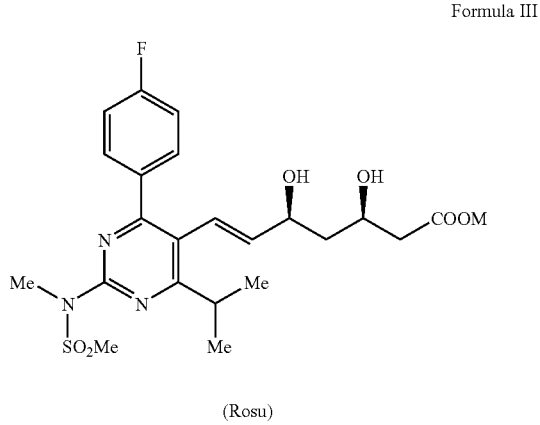

(Rosu)

wherein M is H or a metal cation, preferably $Ca^{+2}$, having about 0.02% to about 0.2% area by HPLC of formula III-ether (Rosu-alkylether).

In another aspect, the present invention provides the use of the compound of formula I-ether, formula II-ether, and Rosu-alkylether as reference standards.

In yet another aspect, the present invention provides a process for determining the amount of: either the compound of formula I-ether in a sample of the compound of formula I, the compound of formula II-ether in a sample of the compound of formula II, or Rosu-alkylether in a sample of Rosu comprising:
 a) measuring by HPLC or TLC the area under a peak corresponding to the compound of formula I-ether, formula II-ether, or Rosu-alkylether, respectively, in a reference standard comprising a known amount of the compound of formula I-ether, formula II-ether, or Rosu-alkylether, respectively;
 b) measuring by HPLC or TLC the area under a peak corresponding to the compound of formula I-ether, formula II-ether, or Rosu-alkylether, respectively, in a sample comprising the compound of formula I and formula I-ether, or the compound of formula II and formula II-ether, or Rosu and Rosu-alkylether, respectively; and
 c) determining the amount of the compound of formula I-ether, formula II-ether, or Rosu-alkylether, respectively, in the sample by comparing the area of step (a) to the area of step (b).

In another aspect, the present invention provides the use of the compound of formula I-ether, formula II-ether, and Rosu-alkylether as reference markers.

In yet another aspect, the present invention provides a process for determining the presence of: either the compound of formula I-ether in a sample of the compound of formula I, the compound of formula II-ether in a sample of the compound of formula II, or Rosu-alkylether in a sample of Rosu comprising:
 a) determining by HPLC or TLC the retention time corresponding to the compound of formula I-ether, formula II-ether, or Rosu-alkylether, respectively, in a reference marker comprising the compound of formula I-ether, formula II-ether, or Rosu-alkylether, respectively;
 b) determining by HPLC or TLC the retention time corresponding to the compound of formula I-ether, formula II-ether, or Rosu-alkylether, respectively, in a sample comprising the compound of formula I and formula I-ether, or the compound of formula II and formula II-ether, or Rosu and Rosu-alkylether, respectively; and
 c) determining the presence of the compound of formula I-ether, formula II-ether, or Rosu-alkylether, respectively, in the sample by comparing the retention times of step (a) to the area of step (b).

In another aspect, the present invention provides an HPLC methodology that includes the steps of: combining a sample of either the compound of formula I, formula II, or Rosu with a mixture of acetonitrile and water at a ratio of 1:1 to obtain a solution; injecting the solution into a 100×4.6 mm BDS Hypersil C-18 (or similar) column, which is maintained at a temperature of about 25° C.; gradually eluting the sample from the column using a mixture of buffer:acetonitrile at a ratio of 3:2 by volume, and acetonitrile and a mixture of buffer:acetonitrile:ethanol at a ratio of 2:9:9 as an eluent; and measuring the amount of either the compound of formula I-ether, formula II-ether, or Rosu-alkylether, respectively, in the relevant sample with a UV detector, preferably at a 243 nm wavelength.

In yet another aspect, the present invention provides a process for preparing the compound of formula I, wherein the level of the compound of formula I-ether is controlled, comprising the steps of: combining a compound of formula IV of the structure,

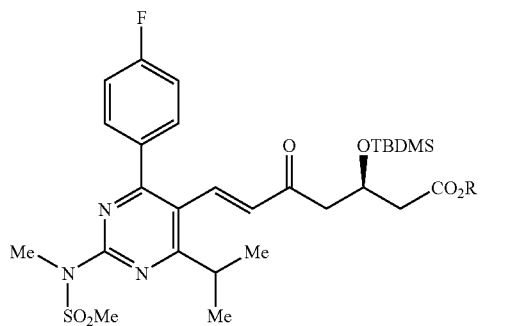

Formula IV with a $C_1$-$C_5$ alcohol to obtain a solution; cooling the solution at a temperature of about −10° C. to about 30° C.; combining the solution of compound IV with a solution of methanesulfonic acid in a mixture of a $C_1$-$C_5$ alcohol:water in a ratio of about 6 to about 30 (v/v) to obtain a reaction mixture; and heating the reaction mixture at a maximum temperature of about 35° C. to obtain the compound of formula I having a controlled level of formula I-ether.

In another aspect, the present invention provides a process for preparing Rosu and salts thereof having about 0.02% to about 0.2% area by HPLC of Rosu-ether by preparing the compound of formula I according to the process described above and converting it to Rosu.

In one aspect, the present invention provide a process for reducing the level of the compound of formula II-ether in a sample of the compound of formula II by a process of crystallization comprising the steps of: combining crude compound of formula II with an organic solvent selected from the group consisting of aromatic hydrocarbons, $C_1$-$C_5$ alcohols, esters, ketones, ethers, $C_5$-$C_8$ linear or branched hydrocarbons, nitrites, mixtures thereof, and mixtures thereof with water, to obtain a reaction mixture; heating the reaction mixture at a temperature of about 25° C. to about 110° C. to obtain a solution; cooling the solution to a temperature of about −10° C. to about 20° C. to induce precipitation of the compound of formula II; and recovering the compound of formula II.

In one aspect, the present invention provides a process for preparing the compound of formula II having about 0.2% to about 0.02% area by HPLC of the compound of formula II-ether by preparing the compound of formula II according to the process described above.

In another aspect, the present invention provides a process for preparing Rosu and salts thereof having about 0.02% to about 0.2% area by HPLC by preparing the compound of formula II according to the process described above and converting it to Rosu.

In yet another aspect, the present invention provides a process for preparing Rosu having about 0.02% to about 0.2% area by HPLC of Rosu-alkylether, comprising:

a) obtaining one or more samples of one or more batches of the compound of formula I;

b) measuring the level of the compound of formula I-ether in each of the samples;

c) selecting a batch of the compound of formula I having a level of formula I-ether of about 0.02% to about 0.2% area by HPLC, based on the measurement of the samples from the batches; and d) using the selected batch to prepare Rosu.

In yet another aspect, the present invention provides a process for preparing Rosu having about 0.02% to about 0.2% area by HPLC Rosu-alkylether, comprising:

a) obtaining one or more samples of one or more batches of the compound of formula II;

b) measuring the level of the compound of formula II-ether in each of the samples;

c) selecting a batch of the compound of formula II having a level of formula II-ether of about 0.02% to about 0.2% area by HPLC, based on the measurement of the samples from the batches; and d) using the selected batch to prepare Rosu.

In yet another aspect, the present invention provides a process for preparing a pharmaceutical formulation comprising Rosu having about 0.02% to about 0.2% area by HPLC of Rosu-alkylether, comprising:

a) obtaining one or more samples of one or more batches of Rosu;

b) measuring the level of the compound of Rosu-alkylether in each of the samples;

c) selecting a batch of Rosu having a level of Rosu-alkylether of about 0.02% to about 0.2% area by HPLC, based on the measurement of the samples from the batches; and d) using the selected batch to prepare a formulation comprising Rosu.

In yet another aspect, the present invention provides a pharmaceutical composition comprising Rosu or salts thereof having about 0.02% to about 0.2% area by HPLC of Rosu-alkylether and at least one pharmaceutically acceptable excipient.

In one aspect, the present invention provides a process for preparing a pharmaceutical composition comprising combining Rosu or salts thereof having about 0.02% to about 0.2% area by HPLC of Rosu-alkylether with at least one pharmaceutically acceptable excipient.

DETAILED DESCRIPTION OF THE INVENTION

The present invention provides rosuvastatin and salts thereof having a low level of impurities, particularly the alkylether impurity of rosuvastatin, and a process for the preparation thereof. The process of the invention allows the preparation of rosuvastatin having a low level of impurities by controlling the level of process impurities arising during the synthesis process. Throughout the synthesis of rosuvastatin, the purity of the reaction product (i.e., the API) is analyzed by HPLC or TLC analysis.

The present invention provides a compound of formula I-ether, having the structure

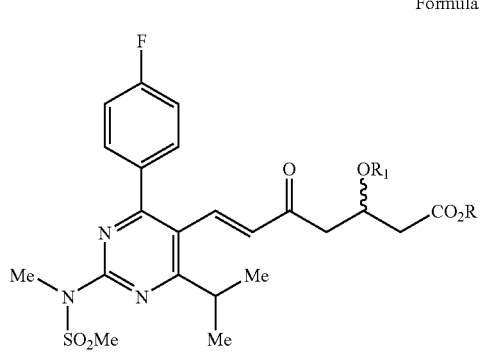

Formula I-ether wherein R is a carboxyl protecting group that is not methyl ester and $R_1$ is a $C_1$-$C_8$ linear or branched alkyl.

The carboxyl protecting group in the structures within the present application may be any suitable carboxyl protecting group, especially esters, amides, or hydrazides. More preferably, the carboxyl protecting group is an ester, and most preferably is tert-butylester in the structures in the present invention.

Formula I-ether is an impurity formed during the conversion of the intermediate compound IV

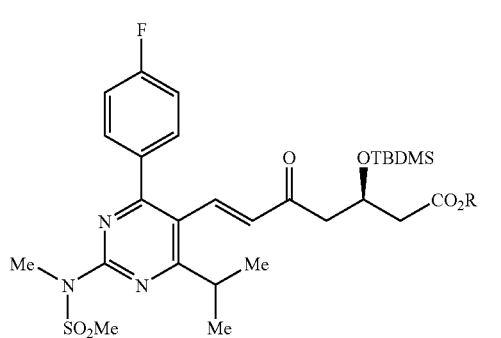

Formula IV wherein R is a carboxyl protecting group, to the compound of formula I:

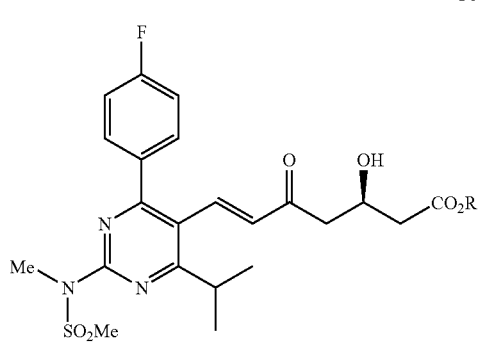

Formula I

The level of formula I-ether can reach as high as about 20% area by HPLC during the conversion of intermediate compound IV to the compound of formula I. The presence of this impurity is problematic because the impurity participates in the remaining steps of the synthesis of Rosuvastatin, leading to other impurities, and eventually, to contaminated Rosuvastatin. The process of the invention controls the level of formula I-ether formed, and provides a method of purifying the intermediate compound of formula II. The invention thus allows the preparation of a final product, Rosuvastatin containing a low level of Rosu-alkylether.

The invention comprises a process of controlling the level of formula I-ether formed during the synthesis of formula I comprising the steps of:

a) combining the compound of formula IV with a $C_1$-$C_5$ alcohol to obtain a solution;
b) cooling the solution at a temperature of about $-10°$ C. to about $30°$ C.;
c) combining the solution of step b) with a solution of methanesulfonic acid in a mixture of a $C_1$-$C_5$ alcohol: water having a ratio of about 6 to about 30 (v/v) to obtain a reaction mixture; and
d) heating the reaction mixture at a maximum temperature of about $35°$ C. to obtain the compound of formula I having a controlled level of the impurity formula I-ether.

Suitable $C_1$-$C_5$ alcohols include methanol, ethanol, propanol, isopropanol, butanol, and amyl alcohol. Preferred alcohols include methanol, ethanol, and isopropanol. Performing the reaction under dilution conditions provides control over the amount of formula I-ether that is formed. Preferably, the solution formed in step a) contains about 13 to about 19 volumes of $C_1$-$C_5$ alcohol per gram of the compound of formula IV, and about 0.5 to about 1 volume of water per gram of formula IV.

The solution is preferably cooled to a temperature of about $0°$ C. to about $20°$ C. in step b). Preferably, the ratio of the $C_1$-$C_5$ alcohol and water mixture in step c) is about 20.6 (v/v). The solution of step b) may be combined with the solution of methanesulfonic in one portion or in sequential portions, such as in a drop-wise manner. Preferably, the solution of methanesulfonic acid in alcohol and water is added drop-wise to the solution of step b) to obtain the reaction mixture. The reaction mixture is preferably formed over a period of about 0.5 hour to about 5 hours, and more preferably over a period of one hour. The temperature is preferably maintained at about $-10°$ C. to about $30°$ C. while forming the reaction mixture. The reaction mixture is then heated to a temperature of no more than $35°$ C., preferably, to about $20°$ C. to about $35°$ C. Controlling the temperature while forming the reaction mixture and during heating of the reaction mixture provides control over the amount of formula I-ether that is formed as a by-product of the reaction.

The reaction mixture preferably is heated at a temperature of about $30°$ C. for about 2 to about 10 hours prior to recovering the compound of formula I.

The compound of formula I can be recovered from the reaction mixture by adding Brine to the reaction mixture at about room temperature, extracting the reaction mixture with an organic solvent, preferably cold toluene, and washing the reaction mixture with a saturated solution of $NaHCO_3$ and with Brine. The organic phase is then dried and concentrated under vacuum.

The compound of formula prepared as described above contains about 0.02% to about 1.5% area by HPLC of the compound of formula I-ether.

The present invention further provides a process for preparing rosuvastatin and salts thereof containing about 0.02% to about 0.2% area by HPLC Rosu-alkylether comprising preparing the compound of formula I as described above, and converting it to rosuvastatin or salts thereof.

The present invention also provides an isolated compound of formula I-ether, wherein R is a carboxyl protecting group, and $R_1$ is a $C_1$-$C_8$ linear or branched alkyl. In a preferred embodiment, R is tert-butyl carboxyl, $R_1$ is methyl, and the compound of formula I-ether corresponds to TB-21-methyl-ether of the structure,

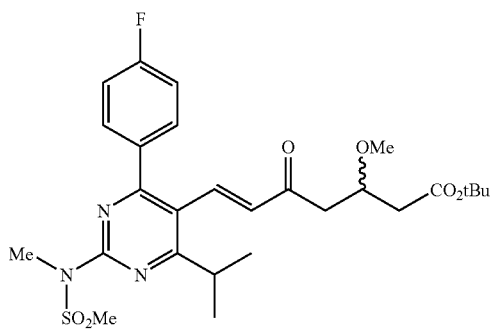

TB-21-methylether

TB21-methylether may be characterized by data selected from: an $^1$H-NMR (CDCl$_3$, 300 MHz) spectrum having peaks at about 1.32, 1.50, 2.43-2.50, 2.71-2.84, 3.40, 4.07, 6.53, 3.61, 6.21 ($J_{Hz}$ 16.5), 7.14, 7.62 and 7.64 ppm; and a $^{13}$C-NMR (CDCl$_3$, 75 MHz) spectrum having peaks at about: 21.84, 28.06, 32.32, 33.09, 40.09, 42.46, 45.68, 57.35, 74.38, 80.90, 115.55 ($J_{Hz}$ 22), 119.07, 132.07 ($J_{Hz}$ 8), 133.57, 133.77 ($J_{Hz}$ 4), 137.48, 157.95, 163.73 ($J_{Hz}$ 251), 164.94, 170.20, 175.39, and 197.06 ppm.

The present invention also provides a process for isolating the compound of formula I-ether from a sample containing formula I and the formula I-ether by flash chromatography. Preferably, the compound of formula I-ether is isolated with a gradient eluent comprising a mixture of heptane and ethylacetate. The isolation of TB21-methylether is exemplified in example 1.

The compound of formula I may be used to prepare rosuvastatin by a process described in co-pending U.S. application Ser. No. 11/360,725. Thus, the compound of formula I is converted into the compound of formula II of the structure:

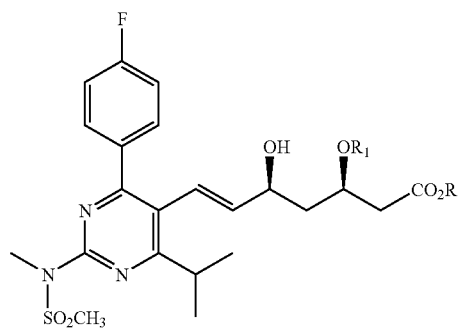

Formula II

The compound of formula II is converted into the compound of formula III (Rosu) or salts thereof:

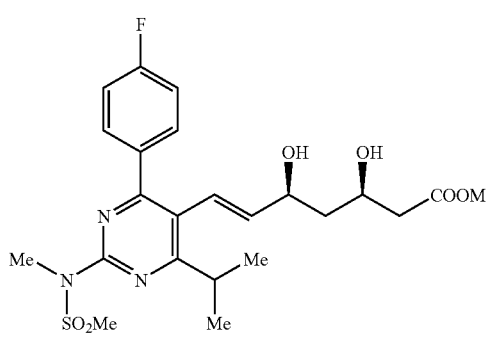

Formula III (Rosu)

wherein M is H or a metal cation, by removing the carboxyl protecting group, as illustrated in the following scheme:

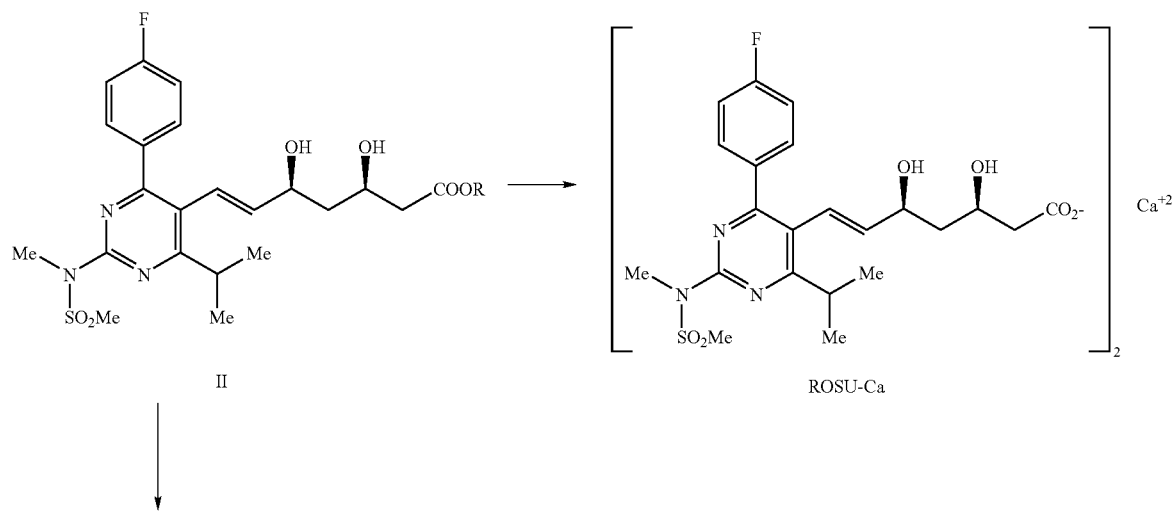

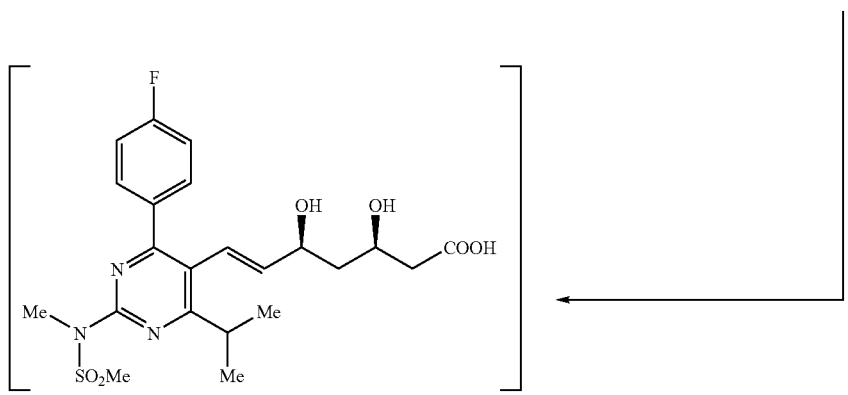

Rosu-Ca$^{+2}$ can be obtained by the process described in co-pending U.S. application Ser. No. 11/360,725 by combining the compound of formula II with a mixture of a $C_1$-$C_6$ alcohol and water to obtain a reaction mixture, and adding a base such as alkali hydroxide to the reaction mixture, preferably portion-wise, to give Rosu-Na$^{2+}$ in situ. Rosu-sodium is then converted to Rosu-Ca$^{2+}$ by addition of CaCl$_2$. Rosu-Ca$^{+2}$ may alternatively be prepared by any other process known to one skilled in the art.

In the process of converting the compound of formula I into the compound of formula II and Rosu, the impurity of formula I-ether is also converted into the respective impurities of formula II and Rosu, namely formula II-ether and Rosu-alklyether.

The present invention provides the compound of formula II-ether, having the structure:

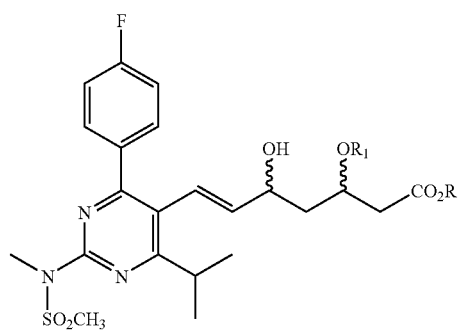

Formula II-ether wherein R is a carboxyl protecting group, and $R_1$ is a $C_1$-$C_8$ linear or branched alkyl; preferably $R_1$ is methyl.

Preferably, R is tert-butyl carboxyl and $R_1$ is methyl, thus, the compound of formula II-ether corresponds to TBRE-methylether having the strucutre,

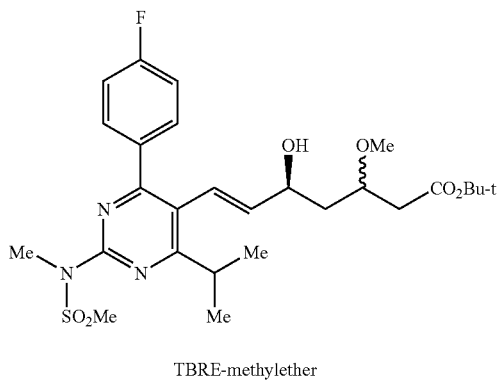

TBRE-methylether

TBRE-methylether may be characterized by data selected from: an $^1$H-NMR (CDCl$_3$, 300 MHz) spectrum having peaks at about 1.28, 1.45, 2.34, 2.40, 2.58, 2.63, 3.34, 3.38, 3.53, 3.60, 4.41, 5.5, 6.62 ($J_{Hz}$ 16.5), 7.10, 7.64 and 7.66 ppm; an $^{13}$C-NMR (CDCl$_3$, 75 MHz) spectrum having peaks at about: 21.74, 28.14, 32.14, 33.19, 39.95, 42.25, 42.5, 57.0, 71, 81.12, 115.0 ($J_{Hz}$ 21.7), 122.58, 132.26, 134.63, 139.61, 140.13, 157.34, 163.32 ($J_{Hz}$ 247.5), 163.50, 174.93 and 174.98 ppm; and a Mass spectra having peaks at: MH+ (ES+): 552.

The present invention also provides the compound of formula II containing about 0.02% to about 1.5% area by HPLC of the compound of formula II-ether and a process for the preparation thereof by crystallization. The process comprises combining crude compound of formula II with an organic solvent selected from the group consisting of aromatic hydrocarbons, $C_1$-$C_5$ alcohols, esters, ketones, ethers, $C_5$-$C_8$ linear or branched hydrocarbons, nitriles, mixtures thereof and mixtures thereof with water, to obtain a mixture, heating the mixture at a temperature of about 25° C. to about 110° C. to obtain a solution, cooling the solution to a temperature of about −10° C. to about 20° C. to induce precipitation of the compound of formula II, and recovering the compound of formula II.

Crude compound of formula II used in the process of the invention may have an assay of about 45% to about 77% area by HPLC. The compound of formula II obtained by the above process typically has an assay of about 80% to about 95% area by HPLC.

Aromatic hydrocarbons suitable for use as an organic solvent include toluene and benzene. Toluene is a preferred aromatic hydrocarbon. Suitable ketones are $C_3$-$C_8$ ketones, and acetone is a preferred ketone. Preferred esters include ethylacetate (referred to as EtOAc) and methylacetate. Preferably, the ether is either tetrahydrofuran or methyl-tertbutylether (referred to as THF and MTBE, respectively). Preferred $C_5$-$C_8$ linear or branched hydrocarbons include heptane and hexane. Preferably, the nitrile is acetonitrile (referred to as ACN). Mixtures of alcohols, acetonitrile, and acetone with water, THF, EtOAc or MTBE, are also suitable organic solvents for use in the invention, as is a mixture of toluene and heptane. The most preferred organic solvent is toluene.

The mixture of crude formula II is preferably heated at a temperature of about 40° C. to about 90° C. to obtain a solution. The solution can be seeded prior to cooling, and is preferably seeded and maintained at a temperature of about 20° C. to about 60° C. for about one hour prior to cooling. Preferably, the solution is cooled to a temperature of about 0° C. to about 5° C. More preferably, the solution is cooled gradually to a temperature of about 40° C. to about 70° C. to obtain a suspension, and then the suspension is further cooled to a temperature of about 0° C. to about 10° C., over a period of about 1 to about 20 hours, to obtain a precipitate of the compound of formula II. When the solution is cooled to obtain a suspension, the suspension is preferably maintained for a period of about 1 hour to about 24 hours, more preferably over night, to obtain a precipitate of the compound of formula II.

The precipitate of the compound of formula II can be recovered by means commonly used in the art, such as by filtering and washing with toluene, preferably cold toluene, and drying in a vacuum oven.

The present invention further provides a process for preparing rosuvastatin and salts thereof, containing about 0.02% to about 0.2% area by HPLC Rosu-alkylether comprising preparing the compound of formula II as described above, and converting it to rosuvastatin or salts thereof.

The present invention further provides the compound of formula III-ether (Rosu-alkylether), having the structure:

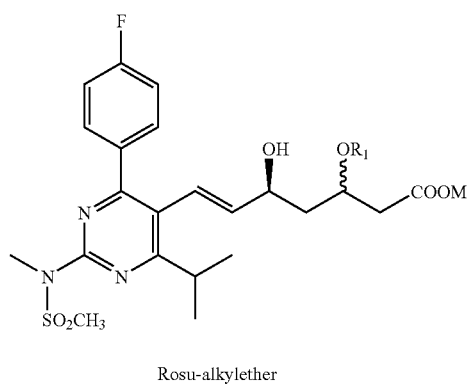

Rosu-alkylether wherein $R_1$ is a $C_1$-$C_8$ linear or branched alkyl, preferably methyl, and M is either H or a metal cation, preferably $Ca^{+2}$.

Preferably, M is $Ca^{+2}$ and $R_1$ is methyl, thus, the compound of formula II-ether corresponds to rosuvastatin calcium methyl-ether having the strucutre,

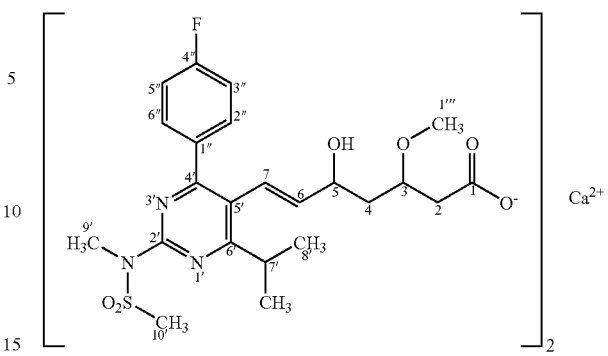

Rosuvastatin calcium methyl-ether

Rosu calcium-methylether may be characterized by data selected from: an $^1$H-NMR (DMSO-$d_6$, 600 MHz) spectrum having peaks at about 1.21, 1.40, 1.70, 2.01, 2.30, 3.13, 3.20, 3.43, 3.45, 3.57, 3.60, 3.74, 4.16, 5.52, 6.51 ($J_{Hz}$ 16.2), 7.28 and 7.71 ppm; and a Mass spectra having peaks at: MH+ (ES+): 496.

The present invention also provides rosuvastatin or salts thereof containing about 0.02% to about 0.2% area by HPLC of Rosu-alkylether.

The present invention provides a process of using the compounds of formula I-ether, formula II-ether, and Rosu-alkylether as reference standards. When used as reference standards, the compounds are useful for determining the amount of either: the compound of formula I-ether in a sample of the compound of formula I, the compound of formula II-ether in a sample of the compound of formula II, or Rosu-alkylether in a sample of Rosu. The process of using the compounds as reference standards comprises:

a) measuring by HPLC or TLC the area under a peak corresponding to the compound of formula I-ether, formula II-ether, or Rosu-alkylether, respectively, in a reference standard comprising a known amount of the compound of formula I-ether, formula II-ether, or Rosu-alkylether, respectively;

b) measuring by HPLC or TLC the area under a peak corresponding to the compound of formula I-ether, formula II-ether, or Rosu-alkylether, respectively, in a sample comprising the compound of formula I and formula I-ether, or the compound of formula II and formula II-ether, or Rosu and Rosu-alkylether, respectively; and c) determining the amount of the compound of formula I-ether, formula II-ether, or Rosu-alkylether, respectively, in the sample of step b) by comparing the area by HPLC or TLC determined in step (a) to the area by HPLC or TLC determined in step (b).

The present invention also a process of using the compounds of formula I-ether, formula II-ether, and Rosu-alkylether as reference markers. When used as reference markers, the compounds are useful in determining the presence of either: the compound of formula I-ether in a sample of the compound of formula I, the compound of formula II-ether in a sample of the compound of formula II, or Rosu-alkylether in a sample of Rosu. The process of using the compounds as reference markers comprises:

a) determining by HPLC or TLC the retention time corresponding to the compound of formula I-ether, formula II-ether, or Rosu-alkylether, respectively, in a reference marker comprising the compound of formula I-ether, formula II-ether, or Rosu-alkylether, respectively;

b) determining by HPLC or TLC the retention time corresponding to the compound of formula I-ether, formula II-ether, or Rosu-alkylether, respectively, in a sample comprising the compound of formula I and formula I-ether, or the compound of formula II and formula II-ether, or Rosu and Rosu-alkylether, respectively; and c) determining the presence of the compound of formula I-ether, formula II-ether, or Rosu-alkylether, respectively, in the sample by comparing the retention times of step (a) to the retention time of step (b).

The present invention provides an HPLC methodology that includes the steps of: combining a sample of either the compound of formula I, formula II or Rosu with a mixture of acetonitrile and water at a ratio of 1:1 to obtain a solution; injecting the solution into a 100×4.6 mm BDS Hypersil C-18 (or similar) column, which is maintained at a temperature of about 25° C.; gradually eluting the sample from the column using a mixture of buffer:acetonitrile at a ratio of 3:2 by volume, and acetonitrile and a mixture of buffer:acetonitrile:ethanol at a ratio of 2:9:9 as an eluent; and measuring the amount of the compound of formula I-ether, formula II-ether or Rosu-alkylether, respectively, in the relevant sample with a UV detector, preferably at a 243 nm wavelength.

Preferably, the buffer contains a mixture of an aqueous solution of glacial acetic acid having a concentration of about 0.05%.

The eluent used is a mixture of eluent A, eluent B, and eluent C, preferably wherein the ratio of the three eluents varies over time, i.e. a gradient eluent. For example, at time 0 minutes, the eluent may contain 100% of eluent A, 0% of eluent B and 0% of eluent C. At 28 minutes, the eluent may contain 60% of eluent A, 40% of eluent B and 0% of eluent C. At 45 minutes, the eluent may contain 0% of eluent A, 0% of eluent B and 100% of eluent C. At 60 minutes, the eluent may contain 0% of eluent A, 0% of eluent B and 100% of eluent C.

The process of the invention for preparing Rosu having about 0.02% to about 0.2% area by HPLC of Rosu-alkylether comprises:

a) obtaining one or more samples of one or more batches of the compound of formula I;

b) measuring the level of the compound of formula I-ether in each of the samples;

c) selecting a batch of the compound of formula I having a level of formula I-ether of about 0.02% to about 0.2% area by HPLC, based on the measurement of the samples from the batches; and d) using the selected batch to prepare Rosu.

If the level of the compound of formula I-ether measured in step b) is higher than about 0.02% to about 0.2% area by HPLC, it may be reduced by converting the compound of formula I to the compound of formula II, according to the process known in the art, followed by reducing the level of the impurity of formula II-ether (which was obtained during conversion) according to the crystallization process described above.

The present invention also provides a process for preparing Rosu having about 0.02% to about 0.2% area by HPLC of Rosu-alkylether, comprising:

a) obtaining one or more samples of one or more batches of the compound of formula II;

b) measuring the level of the compound of formula II-ether in each of the samples;

c) selecting a batch of the compound of formula II having a level of formula II-ether of about 0.02% to about 0.2% area by HPLC, based on the measurement of the samples from the batches; and d) using the selected batch to prepare Rosu.

If the level of the compound of formula II-ether measured in step b) is higher than about 0.02% to about 0.2% area by HPLC, it may be reduced according to the crystallization process described above.

The present invention further provides a process for preparing a pharmaceutical formulation comprising Rosu having about 0.02% to about 0.2% area by HPLC of Rosu-alkylether, comprising:

a) obtaining one or more samples of one or more batches of Rosu;

b) measuring the level of the compound of Rosu-alkylether in each of the samples;

c) selecting a batch of Rosu having a level of Rosu-alkylether of about 0.02% to about 0.2% area by HPLC, based on the measurement of the samples from the batches; and d) using the selected batch to prepare a formulation comprising Rosu.

The present invention also provides a process for preparing a pharmaceutical composition comprising combining Rosu or salts thereof having about 0.02% to about 0.2% area by HPLC of Rosu-alkylether with at least one pharmaceutically acceptable excipient.

Having described the invention with reference to certain preferred embodiments, other embodiments will become apparent to one skilled in the art from consideration of the specification. The invention is further defined by reference to the following nonlimiting examples describing in detail the process of the invention in certain of its embodiments.

EXAMPLES

HPLC Method

| Column: | Hypersil BDS C18 100 × 4.6 mm, 3 mm particle size | | |
|---|---|---|---|
| Diluent: | 50% Water: 50% Acetonitrile | | |
| Mobile phase: | Gradient of Eluent A and Eluent B | | |
| Gradient: | Time (min) | Eluent A(%) | Eluent B(%) | Eluent C(%) |
| | 0 | 100 | 0 | 0 |
| | 28 | 60 | 40 | 0 |
| | 45 | 0 | 0 | 100 |
| | 60 | 0 | 0 | 100 |
| Eluent A: | 60% 0.005M Ammonium Formate buffer 40% Acetonitrile | | |
| Eluent B: | 100% Acetonitrile | | |
| Eluent C: | 10% 0.005M Ammonium Formate buffer 90% Acetonitrile:Ethanol (1:1) | | |
| UV detection: | 243 nm | | |
| Run time: | 60 min | | |
| Flow rate: | 0.4 mL/min | | |
| Injection volume: | 10 mL | | |
| Column temperature: | 25° C. | | |
| Discard limit: | Less than 0.02% | | |
| Sample preparation: | 0.5 mg/mL | | |
| RT of formula I: | about 30.5 min | | |
| RT of formula II: | about 26.2 min | | |
| RT of ROSU: | about 9.0 min | | |

Example 1

Isolation of TB21-Methyl Ester

A reaction mixture containing 20% area by HPLC of the impurity TB21-ether was purified by chromatography (Combiflash Companion, Teledyne Isco). A 4 g column was charged with a 150 mg sample and the sample was eluted with a mixture of solvent A: Heptane, solvent B: EtOAc and detected at $\lambda=245$ nm.

| Time (min.) | Solvent B |
| --- | --- |
| 0-10' | 6% |
| 10'-40' | 6 to 15% |
| 40'-60' | 15% |
| 60'-65' | 15-100% |

The peak detected by combiflash at 40 minutes was analyzed by NMR.

The NMR characterization is as follows:

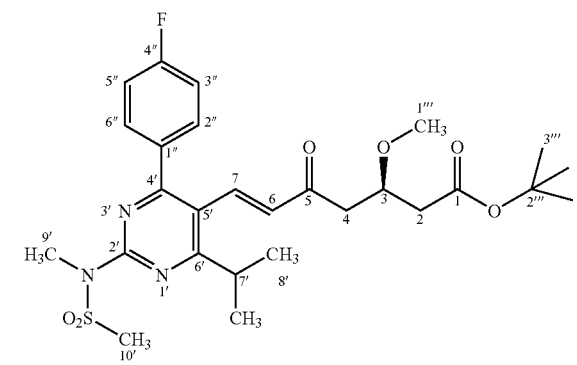

| Number atom | $^1$H NMR CDCl$_3$ δ | J (Hz) | $^{13}$CNMR CDCl$_3$ δ | J (Hz) |
| --- | --- | --- | --- | --- |
| 1 | | | 170.20 | |
| 2 | 2.43 2.50 | | 40.09 | |
| 3 | 4.07 | | 74.38 | |
| 4 | 2.71 2.84 | | 45.68 | |
| 5 | | | 197.06 | |
| 6 | 6.21 | 16.5 | 133.57 | |
| 7 | 7.64 | | 137.48 | |
| 2' | | | 157.95 | |
| 4' | | | 164.94 | |
| 5' | | | 119.07 | |
| 6' | | | 175.39 | |
| 7' | 3.40 | | 32.32 | |
| 8' | 1.32 | | 21.84 | |
| 9' | 3.61 | | 33.09 | |
| 10 | 3.53 | | 42.46 | |
| 1" | | | 133.77 | 4 |
| 2", 6" | 7.62 | | 132.07 | 8 |
| 3", 5" | 7.14 | | 115.55 | 22 |
| 4" | | | 163.73 | 251 |
| 1'" | | | 57.35 | |
| 2'" | | | 80.90 | |
| 3'" | 1.50 | | 28.06 | |

Example 2

Purification of the Compound of Formula II

Crude Formula 11 (22.41 g, assay 76.7%) was stirred in toluene (56 mL). The mixture was heated to about 90° C. until complete dissolution. The solution was then cooled to about 25° C., seeded at this temperature and kept for 1 hour at 25° C. A suspension formed, and was cooled to about 0° C. over 2 hours and stirred at this temperature overnight to obtain a precipitate. The precipitate obtained was filtered, washed with cold toluene (10 mL) and dried at 50° C. in a vacuum oven to get 14.23 g (assay 94.6) of formula II crystals.

| Sample | Formula II | Formula II methyl ether |
| --- | --- | --- |
| crude formula II | 79.42 | 1.24 |
| crystallized formula II | 97.20 | 0.10 |

The NMR characterization is as follows:

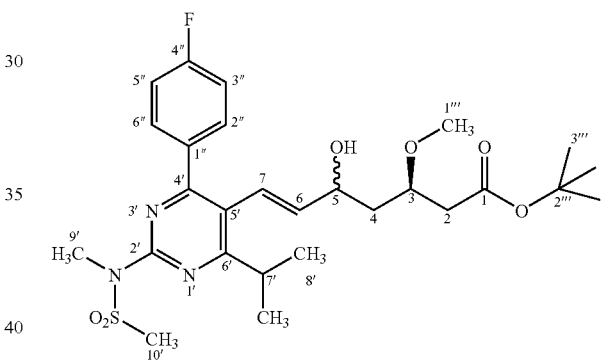

| Number atom | $^1$H NMR CDCL$_3$ δ | J (Hz) | $^{13}$C NMR CDCL$_3$ δ | J (Hz) |
| --- | --- | --- | --- | --- |
| 1 | | | 174.93 | |
| 2 | 2.34 2.40 | | 39.95 | |
| 3 | 4.41 | | 71.0 | |
| 4 | 2.58 2.63 | | 42.5 | |
| 5 | 5.5 | | | |
| 6 | 6.62 | 16 | 139.61 | |
| 7 | 7.64 | | 140.13 | |
| 2' | | | 157.34 | |
| 4' | | | 163.50 | |
| 5' | | | 122.58 | |
| 6' | | | 174.98 | |
| 7' | 3.38 | | 32.14 | |
| 8' | 1.28 | | 21.74 | |
| 9' | 3.60 | | 33.19 | |
| 10' | 3.53 | | 42.25 | |
| 1" | | | 134.63 | |
| 2", 6" | 7.66 | | 132.26 | |
| 3", 5" | 7.10 | | 115.00 | 21.7 |
| 4" | | | 163.32 | 247.5 |
| 1'" | 3.34 | | 57.0 | |
| 2'" | | | 81.12 | |
| 3'" | 1.45 | | 28.14 | |

-continued

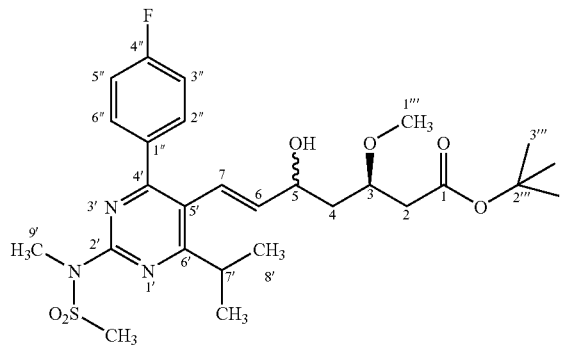

| | ¹H NMR CDCL₃ | | ¹³C NMR CDCL₃ | |
|---|---|---|---|---|
| Number atom | δ | J (Hz) | δ | J (Hz) |

Mass spectra analysis:
MH+ (ES+): 552

Example 3

Crystallization of the Compound of Formula II from ACN:H2O

The compound of formula 11 (1.75 g, containing 0.20% area by HPLC of formula I-methylther) was combined with a mixture of ACN (4.5 ml) and water (3 ml) and heated until complete dissolution. A two layered system was observed, and the mixture was allowed to cool to room temperature, followed by cooling in an ice bath for 18 hrs. The solid was then filtered under reduced pressure, washed, and dried at 50° C. under reduced pressure for 18 hrs to get 1.26 g of formula II containing 0.07% area by HPLC of formula II-ether.

Example 4

Deprotection of the Compound of Formula II to Obtain Rosuvastatin

The compound of formula IV (65.61 g, 52.3% assay) was dissolved in MeOH (650 ml, 10 vol) in a 2 L reactor and cooled to about 10° C. A solution of methanesulphonic acid (3.71 g, 0.73 eq.) in MeOH (590 ml, 9 vol) and H₂O (44 ml, 0.97 vol) was added to the reactor over 1 hour. The resulting mixture was heated to about 30° C. and stirred at this temperature for 10 hours.

The solution was cooled to room temperature. Brine solution (340 ml) was added and a product was extracted with toluene (2×400 ml). Both toluene layers were combined and washed with a saturated solution of NaHCO₃ (340 ml) and brine solution (340 ml). The organic phase was dried over Na₂SO₄ and finally the solvent was removed under reduced pressure to get 46.5 g of viscous oil (assay 50.6%, me-ether 0.81%).

Example 5

Comparative Example: A Repetition of Example 2, Step b of WO 03/097614

The compound of formula IV (3 g, 71.9% assay) was dissolved in MeOH (7.5 ml) and heated to about 34° C. in a flask. A solution of methanesulphonic acid (0.19) in MeOH (7.5 ml) and H₂O (3 ml) was added to the flask. The resulting mixture was stirred at 34° C. for 7.5 hrs.

The mixture was cooled to room temperature. Brine solution (340 ml) was added and a product was extracted with toluene (2×400 ml). Both toluene layers were combined and washed with a saturated solution of NaHCO₃ (340 ml) and brine solution (340 ml). The organic phase was dried over Na₂SO₄ and finally the solvent was removed under reduced pressure to get a viscous oil (2.28 g, assay 50.6%, me-ether 2.01%).

Example 6

Conversion of Formula II into Rosuvastatin Ca with Extraction in Toluene Using Active Carbon A 1 L reactor equipped with a mechanical stirrer was charged with EtOH (100 mL), water (60 ml), and formula II (20 g), forming a reaction mixture. NaOH (47% 1.2 eq, 3.8 g) was added dropwise to the reaction mixture at 25±5° C., and the reaction mixture was stirred at 25±5° C. for two hours.

Water (140 ml) was added to the reaction mixture, and the reaction mixture was washed with toluene (100 mL). The reaction mixture was stirred at 25±5° C. for half an hour and the aqueous phase was isolated.

Active carbon was added to the aqueous phase and the aqueous phase was stirred at 25±5° C. for 30 minutes. The aqueous phase was filtered under reduced pressure with Sinter and Hyflo to eliminate the active carbon present.

The aqueous phase was then concentrated under reduced pressure at 40° C. to half its volume. Water (50 mL) was added to the aqueous phase, forming a solution. The solution was heated to 40° C. CaCl₂ (4.13 g) was added dropwise to this solution over 30-90 minutes at 38-45° C. The solution was then cooled to 25±5° C., stirred at 25±5° C. for 1 hour, filtered, and washed with water (4×20 ml), yielding a powdery compound (16.7 g dry, 90%).

Several experiments have been performed according to this example and the purity profile of these samples is summarized below in Table 1:

TABLE 1

| | Starting material Formula II | | Final material Rosu calcium | |
|---|---|---|---|---|
| Example No. | Purity of Formula II (% area by HPLC) | Formula II Methyl ether (% area by HPLC) | Purity of Rosu (% area by HPLC) | Rosu Methyl ether (% area by HPLC) |
| 1 | 98.4 | 0.14 | 99.6 | 0.04 |
| 2 | 98.4 | 0.09 | 99.62 | 0.03 |
| 3 | 97.3 | 0.16 | 99.02 | 0.02 |
| 4 | 98.3 | 0.10 | 99.55 | 0.04 |

Example 7

Characterization of Rosuvastatin Calcium Methyl Ether

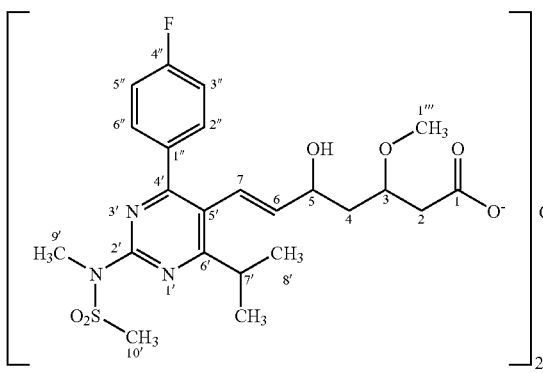

Bruker, 600 MHz

| Number atom | $^1$H NMR DMSO-$d_6$ δ | J (Hz) |
|---|---|---|
| 1 | | |
| 2 | 2.01 | |
|   | 2.30 | |
| 3 | 3.60 | |
|   | 3.74 | |
| 4 | 1.4 | |
|   | 1.7 | |
| 5 | 4.16 | |
| 6 | 5.52 | 16.2 |
| 7 | 6.51 | |
| 2' | | |
| 4' | | |
| 5' | | |
| 6' | | |
| 7' | 3.43 | |
| 8' | 1.21 | |
| 9' | 3.57 | |
| 10' | 3.45 | |
| 1" | | |
| 2", 6" | 7.71 | |
| 3", 5" | 7.28 | |
| 4" | | |
| 1''' | 3.20 | |
|   | 3.13 | |

Mass spectra analysis:
MH+ (ES+): 496

What is claimed is:

1. A process of preparing the compound of formula I having the structure:

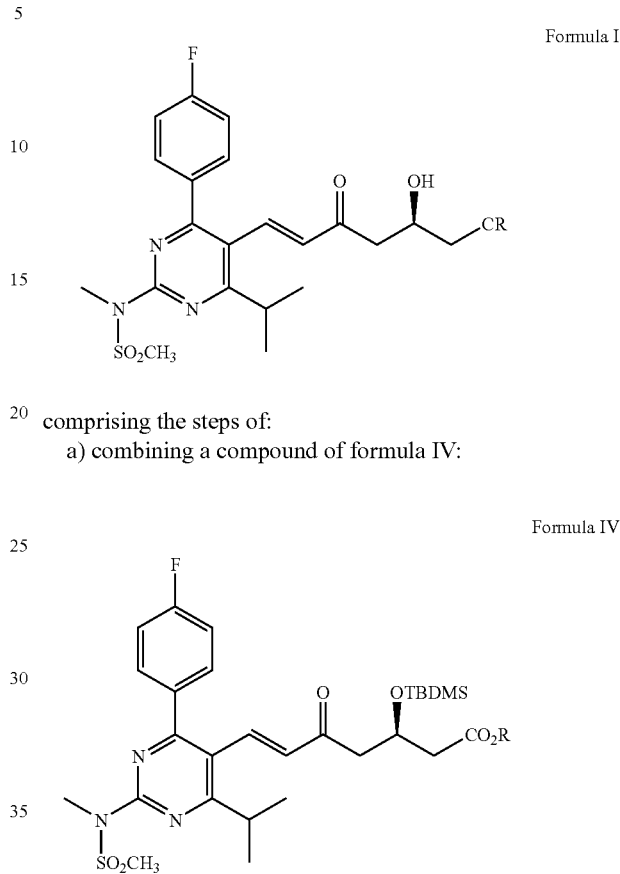

Formula I comprising the steps of:
a) combining a compound of formula IV:

Formula IV wherein R is a carboxyl protecting group, with a $C_1$-$C_5$ alcohol to obtain a solution;
b) cooling the solution at a temperature of about −10° C. to about 30° C.;
c) combining the solution of step b) with a solution of methanesulfonic acid in a $C_1$-$C_5$ alcohol:water mixture having a ratio of about 6 to about 30 (v/v) to obtain a reaction mixture; and
d) heating the reaction mixture at a maximum temperature of about 35° C. to obtain the compound of Formula I.

2. The process of claim 1, wherein the $C_1$-$C_5$ alcohol of step a) is selected from the group consisting of methanol, ethanol, propanol, isopropanol, butanol and amyl alcohol.

3. The process of claim 2, wherein the $C_1$-$C_5$ alcohol of step a) is methanol, ethanol, or isopropanol.

4. The process of claim 1, wherein step b) comprises cooling the solution to a temperature of about 0° C. to about 20° C.

5. The process of claim 1, wherein the $C_1$-$C_5$ alcohol:water mixture in step c) has a ratio of about 20:6 (v/v).

6. The process of claim 1, wherein the solution of methanesulfonic acid in the $C_1$-$C_5$ alcohol:water mixture is added drop-wise to the solution of step b).

7. The process of claim 1, wherein step d) comprises heating the reaction mixture to a temperature of about 20° C. to about 35° C.

8. The process of claim 1, wherein step d) comprises heating the reaction mixture to a temperature of about 30° C.

9. The process of claim 1, wherein step d) comprises heating the reaction mixture for a period of about 2 to about 10 hours.

10. A process of preparing rosuvastatin and salts thereof having about 0.02% to about 0.2% area by HPLC of Rosu-alkylether

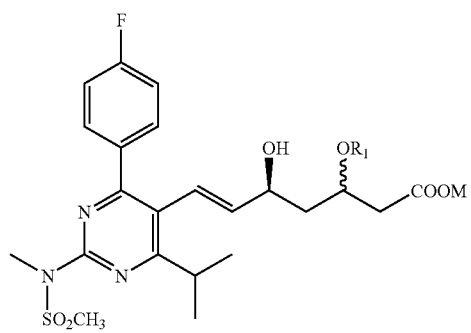

Rosu-alkylether wherein $R_1$ is a $C_1$-$C_8$ linear or branched alkyl, and M is H or a metal cation, comprising carrying out the process of claim 6 and converting the obtained compound to rosuvastatin or a salt thereof.

11. A process of preparing a compound of formula II-ether having the structure:

Formula II-ether

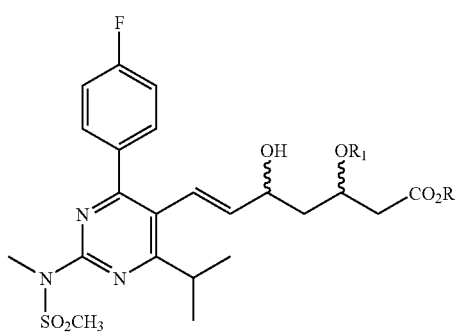

comprising converting the compound of formula I-ether

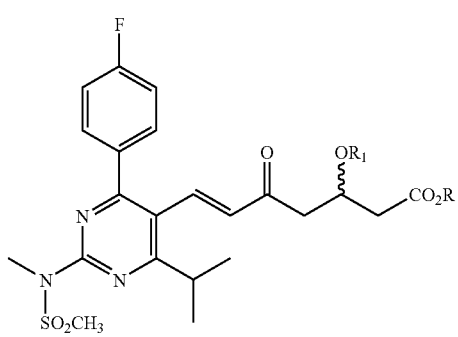

wherein R is a carboxyl protecting group that is not methyl ester and $R_1$ is a $C_1$-$C_8$ linear or branched alkyl, into the compound of Formula II-ether.

12. A process of obtaining a compound of formula II having the structure:

Formula II

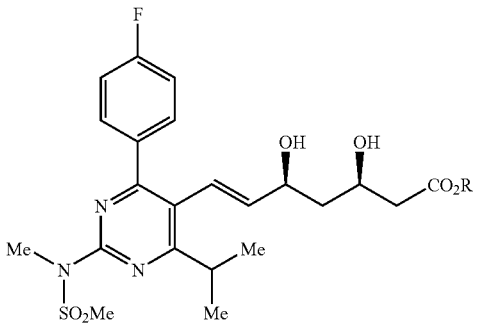

wherein R is a carboxyl protecting group, and $R_1$ is a $C_1$-$C_8$ linear or branched alkyl;

having about 0.02% to about 1.5% area by HPLC of a compound of formula II-ether having the structure:

Formula II-ether

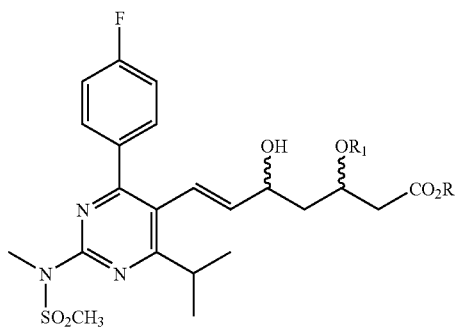

wherein R is a carboxyl protecting group, and $R_1$ is a $C_1$-$C_8$ linear or branched alkyl;

said process comprising:
a) combining the compound of formula II

Formula II

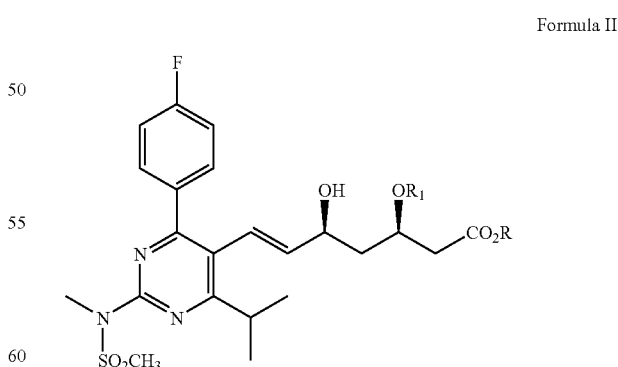

with an organic solvent selected from the group consisting of aromatic hydrocarbons, $C_1$-$C_5$ alcohols, esters, ketones, ethers, $C_5$-$C_8$ linear or branched hydrocarbons, nitrites, mixtures thereof, and mixtures of any of these with water, to obtain a reaction mixture;

b) heating the reaction mixture at a temperature of about 25° C. to about 110° C. to obtain a solution;

c) cooling the solution to a temperature of about −10° C. to about 20° C. to obtain a precipitate; and d) recovering the compound of Formula II.

13. The process of claim 12, wherein the organic solvent is selected from the group consisting of toluene, benzene, acetone, ethylacetate, methylacetate, tetrahydrofuran, methyl-tertbutylether, heptane, hexane, acetonitrile, mixtures of alcohols, acetonitrile, and acetone with water, THF, EtOAc or MTBE, and a mixture of toluene and heptane.

14. The process of claim 13, wherein the organic solvent is toluene.

15. The process of claim 12, wherein step b) comprises heating the reaction mixture at a temperature of about 40° C. to about 90° C.

16. The process of claim 12, further comprising the step of seeding the solution prior to step c).

17. The process of claim 12, wherein step b) further comprises maintaining the solution at a temperature of about 20° C. to about 60° C. for about one hour prior to step c).

18. The process of claim 12, wherein step c) comprises cooling the solution to a temperature of about 0° C. to about 5° C.

19. A process for preparing rosuvastatin and salts thereof having about 0.02% to about 0.2% area by HPLC of Rosu-alkylether of the structure:

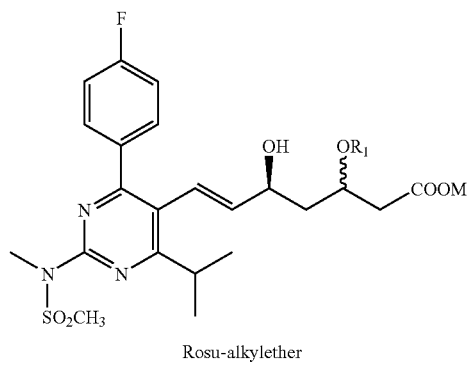

Rosu-alkylether wherein $R_1$ is a $C_1$-$C_8$ linear or branched alkyl, and M is H or a metal cation, said process comprising a) combining a compound of formula II:

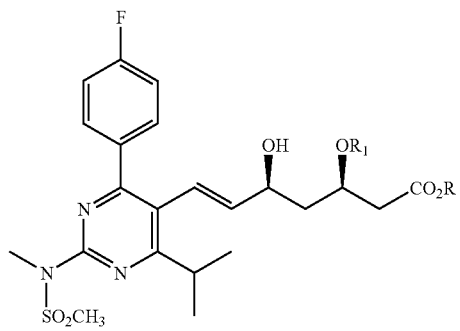

Formula II wherein R is a carboxyl protecting group, and $R_1$ is a $C_1$-$C_8$ linear or branched alkyl, with an organic solvent selected from the group consisting of aromatic hydrocarbons, $C_1$-$C_5$ alcohols, esters, ketones, ethers, $C_5$-$C_8$ linear or branched hydrocarbons, nitrites, mixtures thereof, and mixtures of any of these with water, to obtain a reaction mixture;

b) heating the reaction mixture at a temperature of about 25° C. to about 110° C. to obtain a solution;

c) cooling the solution to a temperature of about −10°0 C. to about 20° C. to obtain a precipitate; and d) recovering the compound of Formula II; and e) converting the recovered compound into rosuvastatin or a salt thereof.

20. A process of preparing the compound of formula III-ether having the structure:

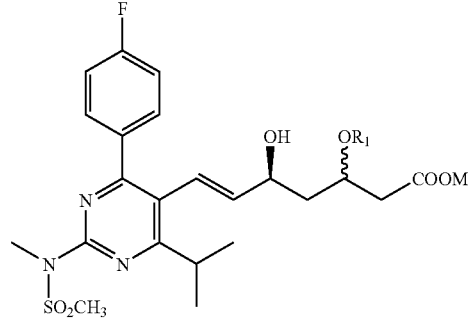

Formula III-ether wherein $R_1$ is a $C_1$-$C_8$ linear or branched alkyl, and M is H or a metal cation;

said process comprising converting the compound of formula II-ether

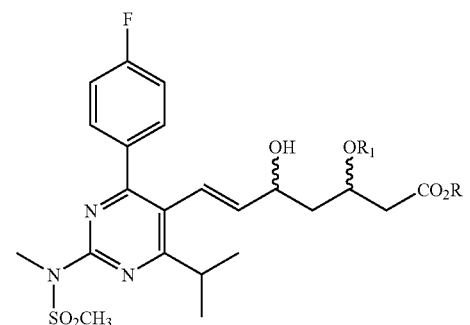

Formula II-ether wherein R is a carboxyl protecting group, and $R_1$ is a $C_1$-$C_8$ linear or branched alkyl, into the compound of formula III-ether.

21. A process for preparing Rosuvastatin or salts thereof having about 0.02% to about 0.2% area by HPLC of the compound of formula III-ether having the structure:

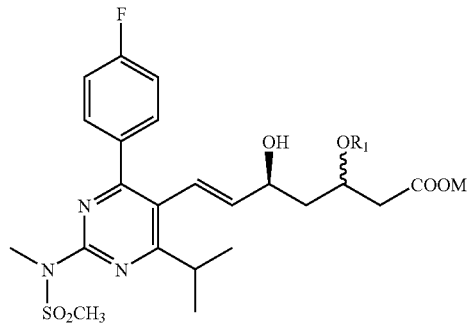

Formula III-ether wherein $R_1$ is a $C_1$-$C_8$ linear or branched alkyl, and M is H or a metal cation, said process comprising the steps of:
 a) obtaining one or more samples of one or more batches of the compound of formula I

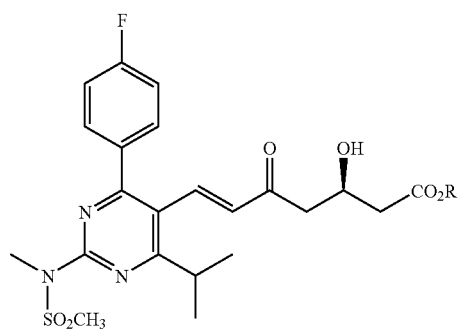

Formula I wherein R is a carboxyl protecting group that is not methyl ester;
 b) measuring the level of the compound of formula I-ether:

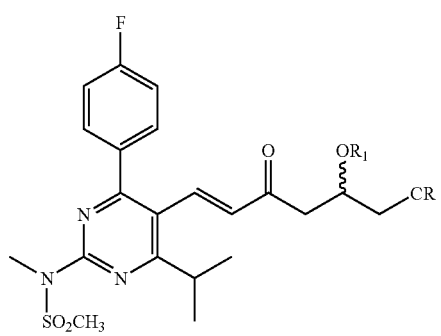

wherein R is a carboxyl protecting group that is not methyl ester and $R_1$ is a $C_1$-$C_8$ linear or branched alkyl in each of the samples;
 c) selecting a batch from step a) having a level of the compound of formula I-ether, in an amount of about 0.02% to about 0.2% area by HPLC, based on the measurement of the samples from the batches; and d) preparing Rosuvastatin having about 0.02% to about 0.2% area by HPLC of the compound of formula III-ether using the selected batch.

22. A process for preparing Rosuvastatin having about 0.02% to about 0.2% area by HPLC of the compound of formula III-ether having the structure:

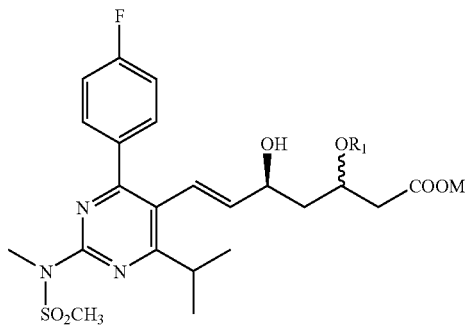

Formula III-ether wherein $R_1$ is a $C_1$-$C_8$ linear or branched alkyl, and M is H or a metal cation, said process comprising the steps of:
 a) obtaining one or more samples of one or more batches of the compound of formula II

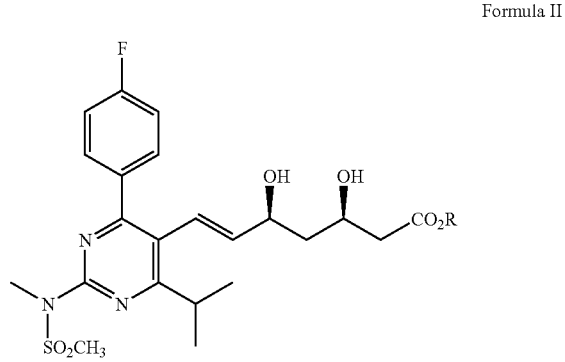

Formula II wherein R is a carboxyl protecting group;
 b) measuring the level in each of the samples of the compound of formula II-ether having the structure:

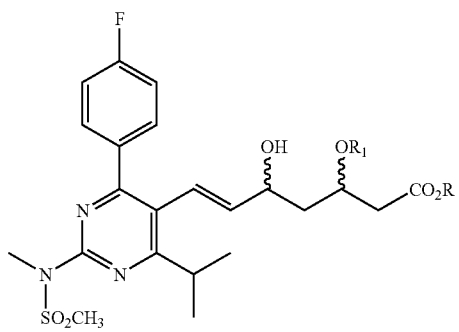

Formula II-ether wherein R is a carboxyl protecting group, and $R_1$ is a $C_1$-$C_8$ linear or branched alkyl;

c) selecting a batch from step a) having a level of the compound of formula II-ether of about 0.02% to about 0.2% area by HPLC, based on the measurement of the samples from the batches; and d) preparing Rosuvastatin having about 0.02% to about 0.2% area by HPLC of the compound of formula III-ether using the selected batch.

23. The process of claim 22, wherein when the level measured in step b) is higher than about 0.02% to about 0.2% area by HPLC, the process further comprises b1) combining the compound of formula II:

Formula II

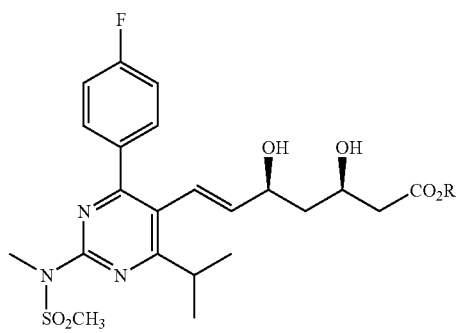

with an organic solvent selected from the group consisting of aromatic hydrocarbons, $C_1$-$C_5$ alcohols, esters, ketones, ethers, $C_5$-$C_8$ linear or branched hydrocarbons, nitriles, mixtures thereof, and mixtures of any of these with water, to obtain a reaction mixture;

b2) heating the reaction mixture at a temperature of about 25° C. to about 110° C. to obtain a solution;

b3) cooling the solution to a temperature of about −10° C. to about 20° C. to obtain a precipitate; and b4) recovering the compound of Formula II containing about 0.02% to about 0.2% area by HPLC of the compound of formula II-ether.

24. A process for preparing a pharmaceutical formulation comprising Rosuvastatin having about 0.02% to about 0.2% area by HPLC of the compound of formula III-ether having the structure:

Formula II-ether

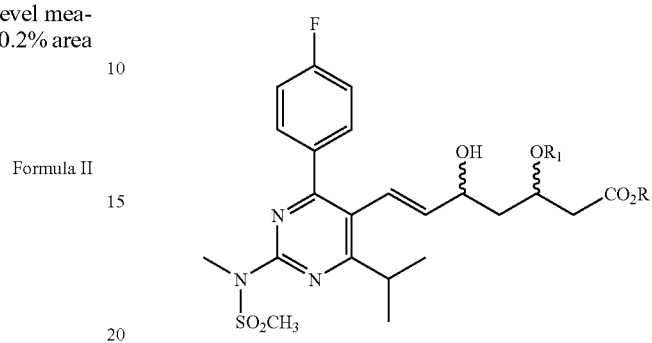

wherein $R_1$ is a $C_1$-$C_8$ linear or branched alkyl, and M is H or a metal cation, said process comprising the steps of:

a) obtaining one or more samples of one or more batches of Rosuvastatin;

b) measuring the level of the compound of formula III-ether in each of the samples;

c) selecting a batch of Rosuvastatin having a level of the compound of formula III-ether of about 0.02% to about 0.2% area by HPLC, based on the measurement of the samples from the batches;

d) preparing Rosuvastatm having about 0.02% to about 0.2% area by HPLC of the compound of formula III-ether using the selected batch; and e) preparing a formulation comprising the Rosuvastatin prepared in step d).

* * * * *

UNITED STATES PATENT AND TRADEMARK OFFICE
CERTIFICATE OF CORRECTION

PATENT NO. : 7,612,203 B2
APPLICATION NO. : 11/360289
DATED : November 3, 2009
INVENTOR(S) : Valerie Niddam-Hildesheim, Anna Balanov and Natalia Shenkar It is certified that error appears in the above-identified patent and that said Letters Patent is hereby corrected as shown below:

At column 5, line 3, please change "R1" to -- $R_1$ --.

At column 5, line 35, please change "R.sub.1" to -- $R_1$ --.

At column 8, line 58, please change "C." to -- C --.

At column 9, lines 23, 28, 44, 45 and 46 please change each occurrence of "C." to -- C --.

At column 12, lines 17-18, 24, 36, 45, 47-48 and 53, please change each occurrence of "C." to -- C --.

At column 14, lines 5-20, please change

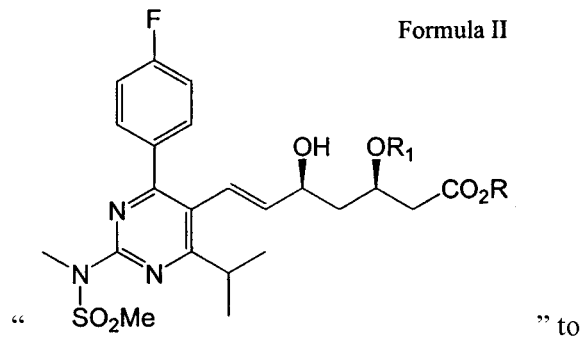

Formula II

" to

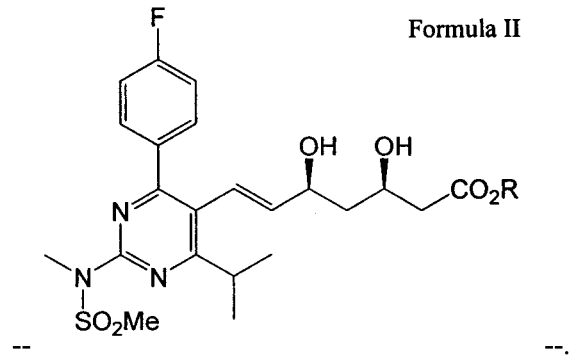

Formula II

--.

Signed and Sealed this
First Day of March, 2011

David J. Kappos
*Director of the United States Patent and Trademark Office*

At column 15, lines 45-60, please change

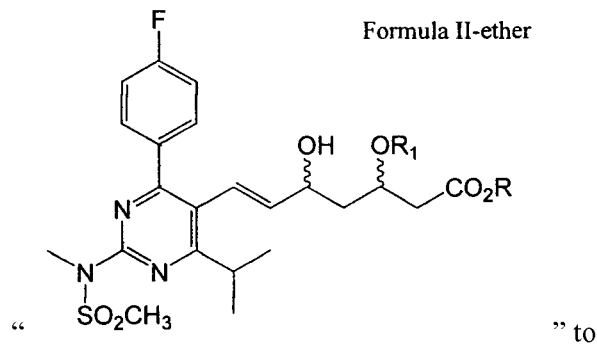

Formula II-ether

" to

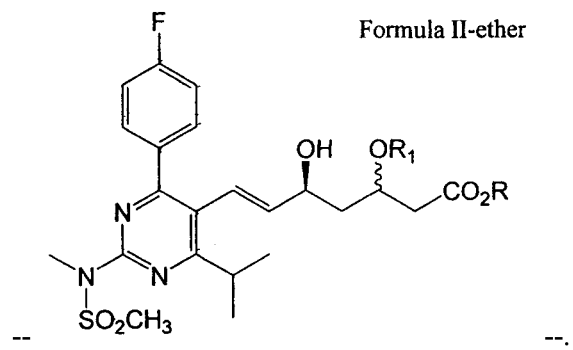

Formula II-ether

--.

At column 16, lines 58 and 60, please change each occurrence of "C." to -- C --.

At column 17, lines 17, 20, 22, 23 and 25, please change each occurrence of "C." to -- C --.

At column 19, line 20, please change "C." to -- C --.

At column 20, line 61, please change "C." to -- C --.

At column 23, lines 42, 54 and 57, please change each occurrence of "C." to -- C --.

At column 24, lines 8, 11, 31, 34, 37, 42 and 46, please change each occurrence of "C." to -- C --.

In claim 1, at column 26, lines 42, 43 and 49, please change each occurrence of "C." to -- C --.

In claim 4, at column 26, line 56, please change the first occurrence of "C." to -- C --.

In claim 7, at column 26, line 63, please change "C." to -- C --.

In claim 12, please delete the text "and $R_1$ is a $C_1$-$C_8$ linear or branched alkyl" beginning at column 28, line 20 and ending at column 28, line 21.

CERTIFICATE OF CORRECTION (continued)
U.S. Pat. No. 7,612,203 B2

Page 3 of 3

In claim 12, at column 28, lines 25 to 40, please change

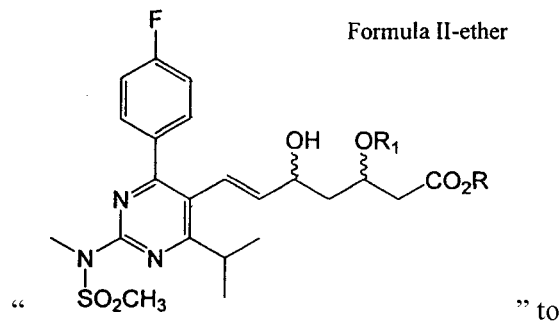

Formula II-ether

"      " to

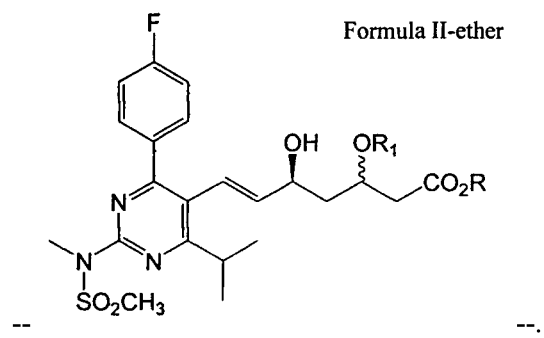

Formula II-ether

--      --.

In claim 23, at column 33, lines 35, 36 and 37, please change each occurrence of "C." to -- C --.

In claim 24, at column 34, lines 5 to 20, please change

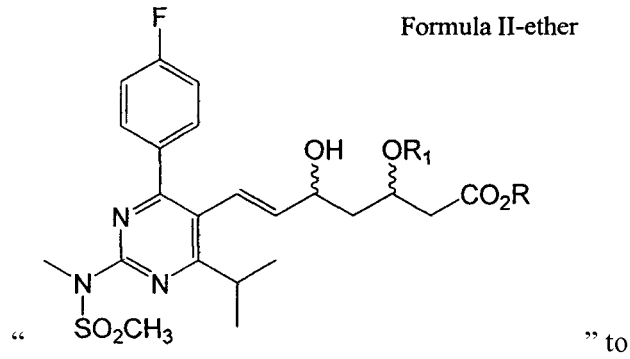

Formula II-ether

"      " to

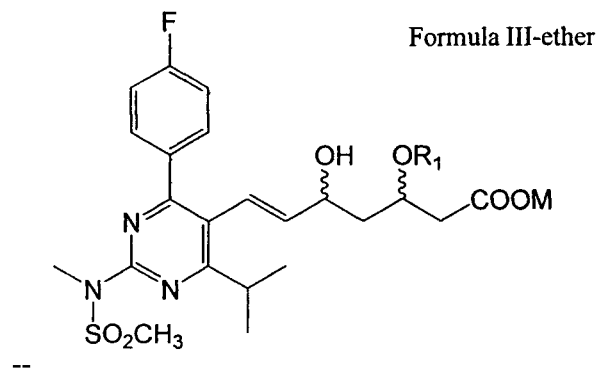

Formula III-ether

--      --.